United States Patent [19]

Iwashita

[11] Patent Number: 5,157,597
[45] Date of Patent: Oct. 20, 1992

[54] METHOD OF DETECTING OSCILLATION OF A SERVO SYSTEM AND AUTOMATICALLY ADJUSTING SPEED LOOP GAIN THEREOF

[75] Inventor: Yasusuke Iwashita, Oshino, Japan
[73] Assignee: Fanuc Ltd., Minamitsuru, Japan
[21] Appl. No.: 571,581
[22] PCT Filed: Dec. 25, 1989
[86] PCT No.: PCT/JP89/01296
  § 371 Date: Aug. 14, 1990
  § 102(e) Date: Aug. 14, 1990
[87] PCT Pub. No.: WO90/07735
  PCT Pub. Date: Jul. 12, 1990

[30] Foreign Application Priority Data

Dec. 23, 1988 [JP] Japan ............................ 63-323692
Jul. 15, 1989 [JP] Japan ............................ 1-181655

[51] Int. Cl.$^5$ ............................................. G05B 13/02
[52] U.S. Cl. ............................ 364/157; 364/163; 364/174; 318/561
[58] Field of Search ............... 364/157, 158, 159, 160, 364/161, 162, 163, 148, 553, 174; 318/561, 609, 610, 611, 615–618, 620, 632

[56] References Cited

U.S. PATENT DOCUMENTS

| | | | |
|---|---|---|---|
| 4,549,123 | 10/1985 | Hagglund et al. ............... | 364/157 X |
| 4,669,040 | 5/1987 | Pettit et al. .................... | 364/162 |
| 4,754,391 | 6/1988 | Suzuki ............................ | 364/157 |
| 4,758,943 | 7/1988 | Astrom et al. .................. | 364/157 |
| 4,855,674 | 8/1989 | Murate et al. .................. | 364/157 X |
| 4,881,160 | 11/1989 | Sakai et al. .................... | 364/157 X |

Primary Examiner—Joseph Ruggiero
Attorney, Agent, or Firm—Staas & Halsey

[57] ABSTRACT

Method for automatically detecting oscillation of a servo system, and for rapidly, correctly and automatically adjusting a speed loop gain thereof.

The servo system is operated with the position loop gain set to a large value, to rotate a motor in forward and reverse directions in an oscillating fashion. In an oscillation detection process, various frequency components of a speed signal (Vt) are repeatedly derived by Fourier transformation while the speed loop gains (k1, k2) are increased, and a main oscillation component (fmax) having a maximum amplitude among the frequency components is repeatedly determined (201, 202), and when the main oscillation component has rapidly increased (204, 209), it is determined that an oscillation of the servo system attributable to the resonance of a mechanical system has occurred and a warning is displayed. In a gain adjustment process, if the main oscillation component assumes a value close to a reference frequency (fa) during the motor oscillation in an integral-plus-proportional control or proportional-plus-integral control mode while the speed loop gain is changed, the loop gain and control mode (P) at that time are fixedly set (303), and if the main oscillation component does not fall in the vicinity of the reference frequency in the proportional-plus-integral control, a loop gain derived based on the upper limit cut-off frequency ($f_{lim}$) is settled (311).

12 Claims, 7 Drawing Sheets

METHOD OF DETECTING OSCILLATION OF A SERVO SYSTEM AND AUTOMATICALLY ADJUSTING SPEED LOOP GAIN THEREOF

TECHNICAL FIELD

The present invention relates to a method of detecting the oscillation of a servo system which is provided in various machines equipped with servomotors, such as a machine tool, robot, etc., and automatically adjusting the speed loop gain thereof.

BACKGROUND ART

In general, a servo system comprises a speed control loop for generating a torque command corresponding to the difference between a command speed from a position control loop and an actual motor speed. The speed control loop of a typical servo system shown in FIG. 1 is arranged to effect a proportional-plus-integral control or integral-plus-proportional control when a parameter P assumes a value of "1" or "0", respectively. In FIG. 1, symbols Vc and Tc respectively denote a speed command signal and an actual speed signal; k1 and k2, an integral gain and a proportional gain; kt, denotes a torque constant; and Jm, rotor inertia.

The speed control loop in FIG. 1 is a secondary control system and the response characteristic thereof is determined in dependence on the speed loop gain. That is, when the loop gain is excessively small, the motor rotation will not immediately follow each of movement command pulses supplied from the servo system and a control lag occurs in such a way that the motor cannot start rotating before a plurality of pulses are accumulated, thus causing a low-frequency undulation in the motor speed. Further, the servo system is liable to be affected by disturbance. On the other hand, when the loop gain is excessively large, the control stability is degraded. If the loop gain is further increased, a mechanical system drivingly coupled to the servomotor resonates and causes an oscillation in the servo system. In this case, in machine tools, for example, vibration occurs even at the time of cutting and feeding operation at a normal motor speed.

Therefore, it is necessary to appropriately set the loop gain, i.e., the integral gain k1 and the proportional gain k2, and more specifically, both the gains k1 and k2 must be set to a large value falling within a range in which no oscillation occurs in the servo system. To this end, in view of the fact that the gain k1 varies as a function of a cut-off frequency fn and the gain k2 varies as a function of the cut-off frequency fn and a damping factor (attenuation factor) ξ, as indicated in the following equations (1) and (2), conventionally, the parameters fn and ξ for each machine equipped with the servo system are set in a trial and error manner, for appropriate determination of the loop gain.

$$k1 = (Jm/Kt) \cdot (2\pi fn)^2 \quad (1)$$

$$k2 = (Jm/Kt) \cdot 2\xi \cdot 2\pi fn \quad (2)$$

Therefore, it requires much effort and a long time to determine the loop gain.

DISCLOSURE OF THE INVENTION

An object of the present invention is to provide an automatic adjusting method capable of rapidly and correctly determine the speed loop gain of the servo system.

Another object of the present invention is to provide a detection method capable of automatically detecting the oscillation of the servo system.

To achieve the above objects, according to one aspect of the present invention, there is provided a method of automatically adjusting a speed loop gain of a servo system comprising the steps of: (a) setting a position deviation-to-position loop gain characteristic of the servo system such that the position loop gain of the servo system assumes a large value in a predetermined position deviation range; (b) periodically extracting a position deviation parameter generated when the servo system is operated in accordance with a position command falling within the predetermined position deviation range; (c) determining a main oscillation component of the position deviation parameter; and (d) automatically adjusting the speed loop gain of the servo system such that the main oscillation component falls within a predetermined frequency range.

According to another aspect of the present invention, there is provided a method of detecting an oscillation of a servo system, which comprises the above steps (a) to (c); a step of executing the steps (b) and (c) after increasing the speed loop gain of the servo system; and a step of automatically determining that oscillation has occurred in the servo system when the main oscillation component has rapidly increased.

As described above, according to the present invention, the speed loop gain of the servo system is automatically adjusted such that the main oscillation component of the position deviation parameter, determined on the basis of the parameter periodically extracted during operation of the servo system having a position deviation-to-position loop gain characteristic which is set so that the position loop gain assumes a large value in the predetermined position deviation range, falls within the predetermined frequency range, and it is automatically determined that oscillation has occurred in the servo system when the main oscillation component of the position deviation parameter has rapidly increased with an increase in the the speed loop gain of the servo system. Accordingly, the speed loop gain can be rapidly and appropriately determined, and thus an optimum speed loop gain can be easily obtained even when a secular change has occurred in the mechanical system or when the inertia of the mechanical system has changed.

BEST MODE OF CARRYING OUT THE INVENTION

Figure 1:
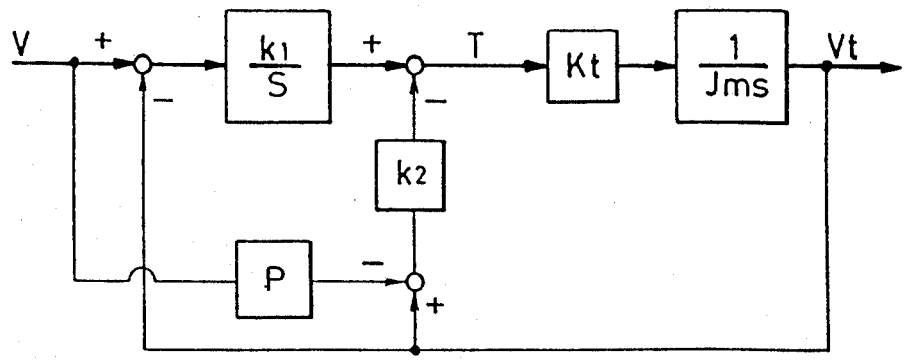
FIG. 1 is a function block diagram showing a speed control loop of a conventional servo system.
Figure 2:
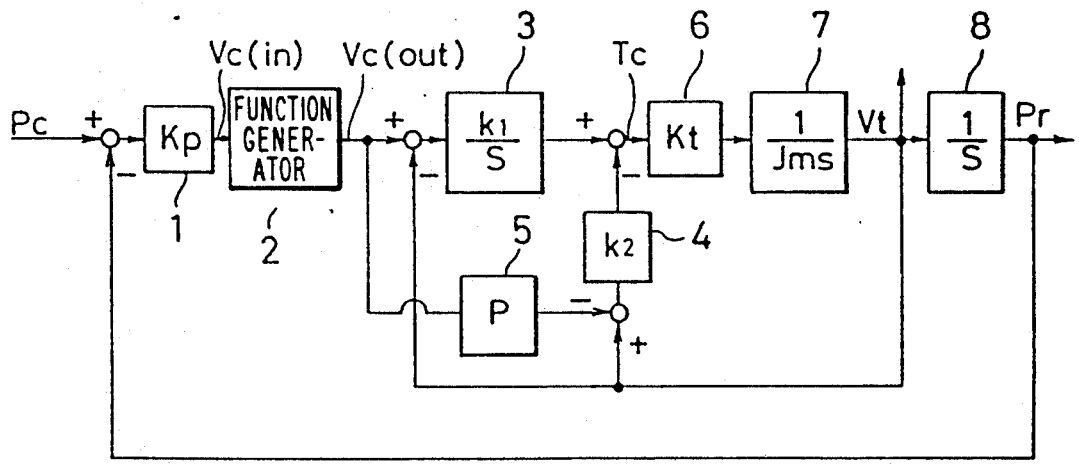
FIG. 2 is a function block diagram showing a position control loop and a speed control loop of a servo system to which an automatic speed loop gain adjusting method according to a first embodiment of the present invention is applied.

A digital servo system, to which an automatic speed loop gain adjusting method according to one embodiment of the present invention is applied, comprises a numerical control unit (whose function is shown in FIG. 2) for effecting a servo control by a software processing, and is arranged to achieve the function equivalent to that of the speed control loop of FIG. 1. The digital servo system is characterized by a function generating ability (hereinafter referred to as a function generator 2), mentioned later, for automatic adjustment of the speed loop gain. In FIG. 2, the elements denoted by reference numerals 3 to 7 respectively correspond to those already explained with reference to FIG. 1, and a description thereof is partly omitted.

The operation of the digital servo system will be explained below.

During the execution of the position control loop process by the digital servo system, a position signal Pr indicative of the actual rotation position of the servomotor is created in an integration term 8. Then, the difference (position deviation) between the position signal Pr and the position command Pc is amplified in a proportional term 1 having a gain of Kp, and a first speed command Vc(in) corresponding to the position deviation is created.

In a normal operation of the servomotor (not shown), the speed control loop process, mentioned later, is executed in accordance with the first speed command Vc(in). On the other hand, at the time of a gain adjustment, the command Vc(in) is converted into a second speed command Vc(out) according to the following equations (3) and (4), in the function generator 2 having a conversion characteristic (position deviation-to-position loop gain characteristic) shown in FIG. 3.

$$Vc(out) = K \cdot Vc(in) + A \text{ (when } Vc(in) \geq 0) \quad (3)$$

$$Vc(out) = K \cdot Vc(in) - A \text{ (when } Vc(in) < 0) \quad (4)$$

Figure 3:
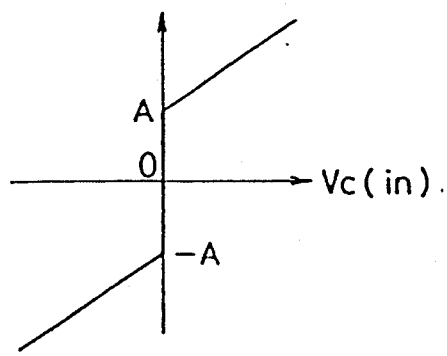
FIG. 3 is a diagram showing a conversion characteristic of a function generator of FIG. 2.

Here, symbol A indicates an offset value which the command Vc(out) takes at a point of Vc(in)=0 when the command Vc(in) approaches a value "0" from the positive side, −A indicates an offset value which the command Vc(out) takes at a point of Vc(in)=0 when the command Vc(in) approaches a value "0" from the negative side, and K indicates the gradient of the characteristic curve of FIG. 3.

Accordingly, at the time of speed loop gain adjustment, unlike the normal motor operation, the second speed command Vc(out) takes a large value even when the first speed command Vc(in) or position deviation has a value of or close to zero. In other words, at the time of the gain adjustment, the position loop gain assumes a considerably large value, as compared with the case of the normal operation, in a position deviation range in which the position deviation has a value or close to zero.

In the speed control loop process following the above position control loop process, the difference (speed deviation) between a speed signal Vt indicative of the actual motor speed and the speed command Vc(in) or Vc(out) is integrated in an integration term 3. In the case where a parameter P is set to the value "1" to effect the proportional-plus-integral control, the torque command Tc becomes equal to a value which is obtained by subtracting the product of a value obtained by subtracting the speed command Vc(out) from the speed signal Vt and the proportional gain k2, from the integrated value of the speed deviation. On the other hand, in the case where the parameter P is set to the value "0" to effect the integral-plus-proportional control, the torque command becomes equal to a value obtained by subtracting the product of the speed signal Vt and the proportional gain k2 from the integrated value of the speed deviation. Then, the current control loop process is effected in accordance with the torque command, whereby the servomotor is driven and controlled.

Figure 4:
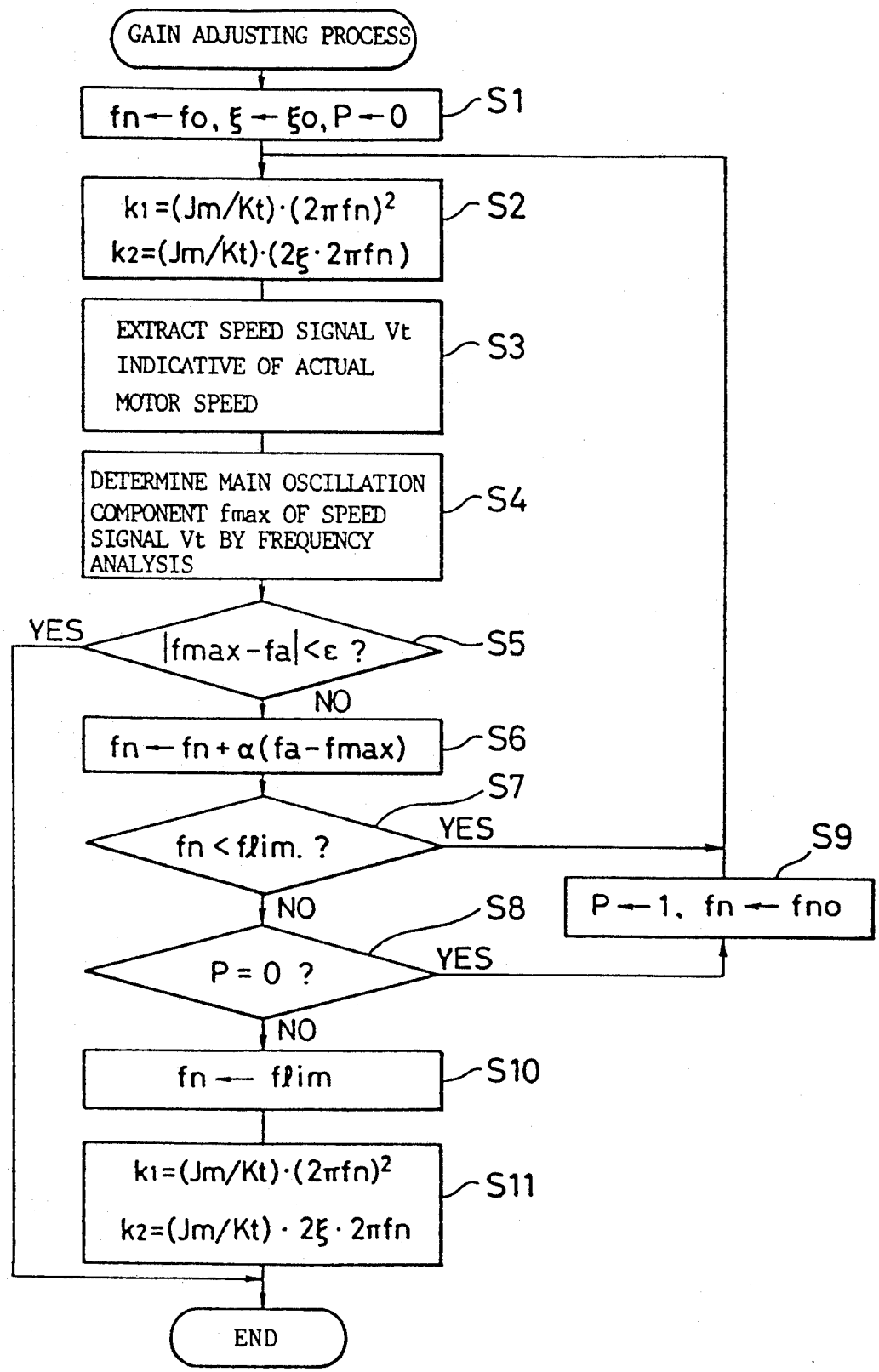
FIG. 4 is a flowchart illustrating an automatic speed loop gain adjusting process effected by the servo system of FIG. 2.

With reference to FIG. 4, the automatic speed loop gain adjusting process effected by the numerical control unit of the digital servo system will be now explained in detail.

At first, an operator operates a data input device (not shown) of the numerical control unit to set the cut-off frequency fn, damping factor ξ and parameter P to initial values fn0, ξ0 and "0", respectively, and to set gain adjusting parameters such as a reference frequency fa, mentioned later. Thereafter, when the operator changes the operation mode of the numerical control unit to an automatic gain adjusting mode, the processor of the numerical control unit stores the setting values fn0, ξ0, "0", fa, etc., into a memory accommodated in the unit (step S1). Next, the processor derives the loop gain, i.e., integral gain k1 and proportional gain k2, in accordance with the equations (1) and (2) and based on the setting values fn0 and ξ0, and the torque constant Kt and rotor inertia Jm previously set, and stores the derived loop gain (step S2).

Whereupon, the numerical control unit starts the foregoing speed control loop process, with the position command Pc set to a value of "0". At this time, even if the position command Pc is set to the value "0", a slight position deviation usually occurs in a positive or negative direction. The processor performs a required arithmetic operation in accordance with the equations (3) and (4), to achieve the function of the function generator 2 having the conversion characteristic shown in FIG. 3, and convert a first speed command Vc(in), having a small positive or negative value corresponding to the slight position deviation, into a second speed command Vc(out) having a considerably large positive or negative value. As apparent from the equation (3), even if the position deviation is zero, the command Vc(out) assumes a large positive value.

As a result, the servomotor which is driven in accordance with the command Vc(out) rotates (stick slip) in a positive or negative direction against friction caused in the motor driving mechanism, and reaches a rotation position which is considerably deviated from a rotation position corresponding to the position command of zero. At the rotation position thus reached, there occurs a considerably large position deviation having a sign opposite to that of the original position deviation. Accordingly, a relatively large speed command Vc(out) having a sign opposite to that of the original speed command Vc(out) is transmitted, so that the servomotor rotates in the reverse direction to a rotation position which is considerably deviated from the rotation position corresponding to the command position of zero. After all, the servomotor repeats the forward and reverse rotations (hereinafter referred to as motor oscillation) in an oscillating fashion. At this time, as the frequency band of the speed control loop determined as a function of the cut-off frequency fn is set in a higher frequency range, that is, as the response of the speed control loop is higher, the motor oscillation frequency becomes higher.

In the motor oscillation, the processor periodically extracts a speed signal Vt indicative of the actual motor speed over a predetermined period of time (step S3), and carries out frequency analysis such as Fourier transformation for the extracted speed signal group (step S4). In the frequency analysis, a frequency component (hereinafter referred to as a main oscillation component fmax) having the maximum amplitude among various frequency components of the speed signal Vt is extracted. That is, the frequency components of the signal Vt, attributable to the friction in the motor driving system, etc., are removed, and the frequency component of the signal Vt which corresponds to the speed command Vc(out) and the motor oscillation is extracted.

Next, the processor determines whether or not the absolute value |fmax−fa| of the difference between the main oscillation component fmax and a reference frequency fa is smaller than a threshold value $\epsilon$ for gain adjustment (step S5). The reference frequency fa is set beforehand to an optimum value for the speed loop gain adjustment, which is determined on the basis of the experience of the operator and the like, and the threshold value $\epsilon$ is set beforehand to approximately 1 Hz. If the absolute value |fmax−fa| is smaller than the threshold value $\epsilon$, the gain adjustment process of FIG. 4 is completed.

In general, it is determined at step S5 that the absolute value |fmax−fa| is larger than the threshold value $\epsilon$, and the cut-off frequency fn is updated (step S6). That is, the processor adds the product $\alpha$ (fa−fmax) of a value obtained by subtracting the main oscillation component fmax from the reference frequency fa and an arithmetic coefficient $\alpha$ which is previously set to approximately 0.5 to 0.7, to the present cut-off frequency fn (which is initially set to the initial value fn0), and then sets the result fn+$\alpha$ (fa−fmax) of addition as a new cut-off frequency fn.

Further, the processor determines whether or not the updated cut-off frequency fn is smaller than a predetermined value $f_{lim}$ indicative of the upper limit of the frequency band of the speed control loop (step S7), and if the value fn is smaller than the value $f_{lim}$, step S2 is entered. Then, the processor executes the foregoing process of step S2 and later steps. On the other hand, if the cut-off frequency fn is larger than the upper limit $f_{lim}$ of the frequency band, the processor determines whether or not the value of parameter P is equal to "0" (step S8). If the value of parameter P is "0", the processor sets the parameter P and the cut-off frequency fn to the value "1" and the initial value fn0 (step S9), respectively, and then step S2 is entered.

During the execution of steps S2 to S9, if it is determined at step S5 that the absolute value |fmax−fa| is smaller than the threshold value $\epsilon$, the processor determines the currently set values of the integral gain k1, proportional gain k2 and parameter P as adjusted values of the parameters k1, k2 and P, and completes the gain adjustment process of FIG. 4.

Further, during repetitive execution of steps S2 to S7 after the parameter P is changed from the value "0" to the value "1", if the cut-off frequency fn becomes larger than the upper limit $f_{lim}$ of the frequency band before the absolute value |fmax−fa| becomes smaller than the threshold value $\epsilon$, then the determination result at step S8 becomes negative. In this case, step S10 is entered to set the cut-off frequency fn to the upper limit $f_{lim}$ of the frequency band, and to determine the gains k1 and k2 based on the thus set cut-off frequency fn (=$f_{lim}$) (step S11), whereby the gain adjustment is completed. As a result of the process of steps S5 to S11, an occurrence of oscillation in the speed control loop is determined when the motor oscillation frequency fmax is high, and the gains k1 and k2 are effectively reduced. This makes it possible to prevent the speed loop gain from being excessively large even in such a case.

In the normal operation of the servomotor after the gain adjustment, the function generator 2 of the servo system is rendered inoperative, and therefore, a speed command corresponding to the first speed command Vc(in) is supplied from the position control loop to the speed control loop. Then, the speed control loop of the servo system effects the proportional-plus-integral control or integral-plus-proportional control in dependence on the value of parameter P, which is determined in the above manner, with the use of the integral gain k1 and proportional gain k2 determined as explained above. As a result, an optimum speed control ia carried out with the large control gain and without causing oscillation in the servo system.

Figure 5:
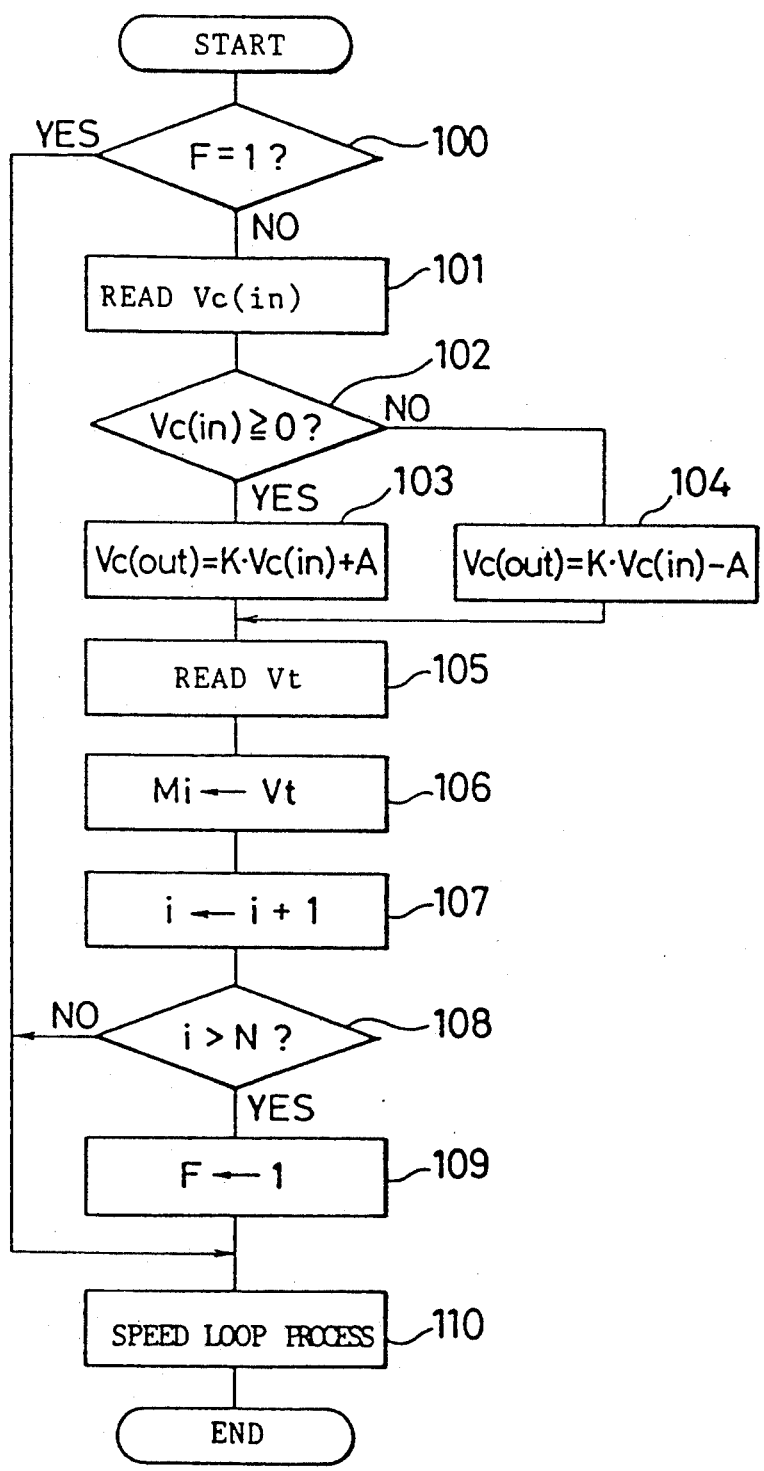
FIG. 5 is a flowchart illustrating an actual motor speed detection process and speed control loop process according to a second embodiment of the present invention.
Figure 6:
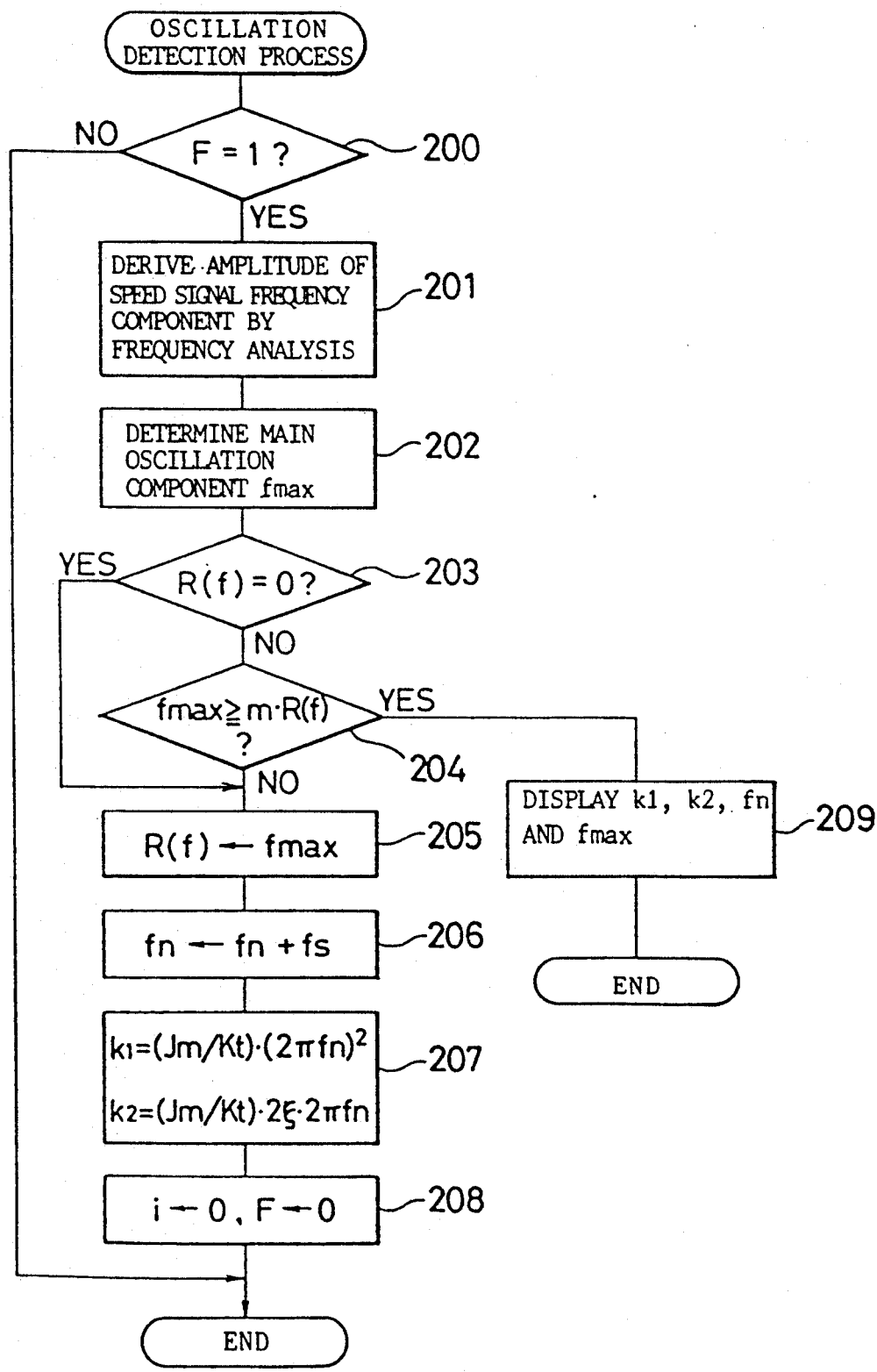
FIG. 6 is a flowchart illustrating an oscillation detection process according to the second embodiment.
Figure 7:
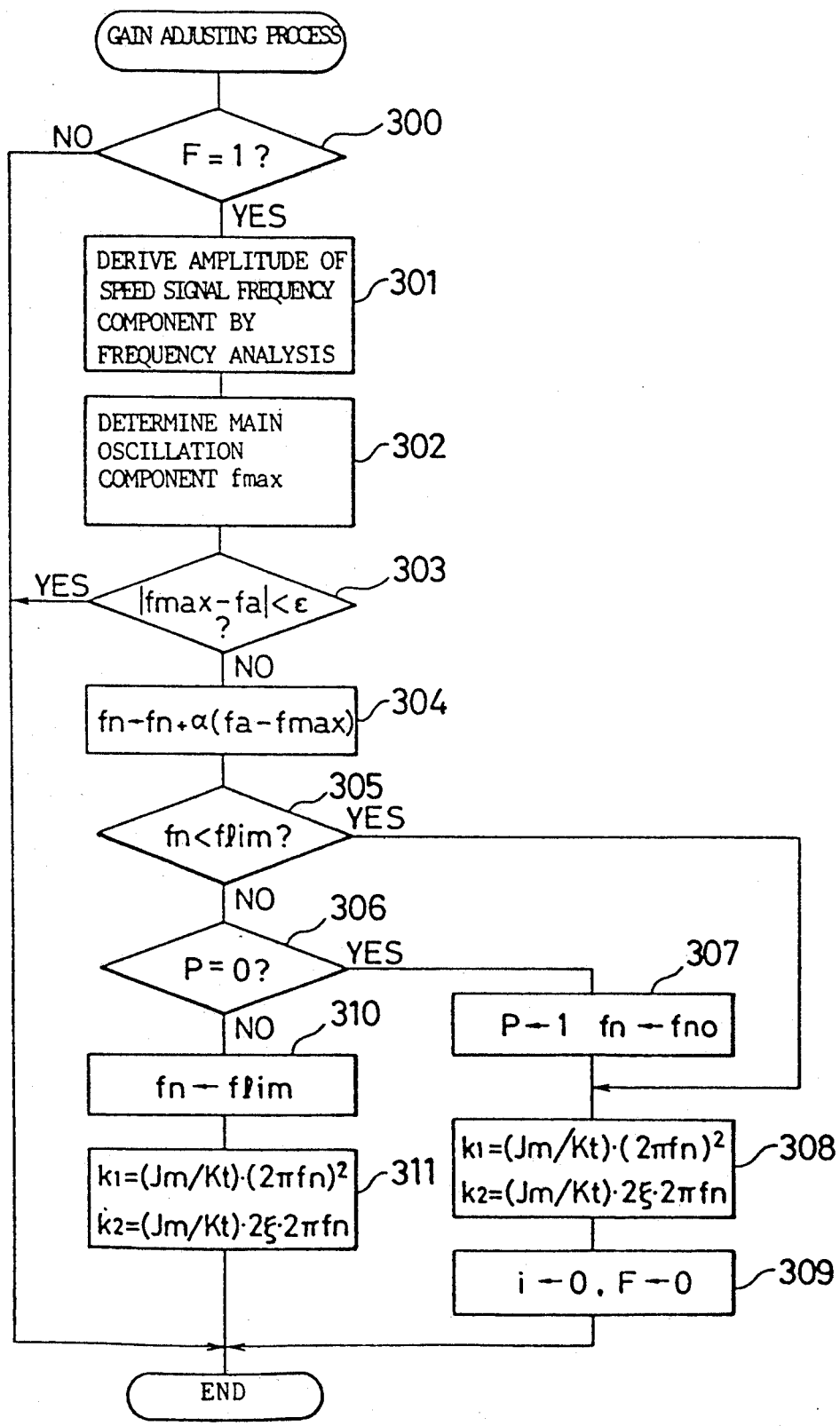
FIG. 7 is a flowchart illustrating a gain adjusting process according to the second embodiment.

With reference to FIGS. 5-7, a method of detecting oscillation of a servo system and automatically adjusting the speed loop gain thereof, according to a second embodiment of the present invention, will be described.

A numerical control unit for embodying the method of the present embodiment is constructed in substantially the same manner as the unit of the first embodiment. The numerical control unit of the present embodiment is characterized in that the same unit is operable in a detection mode for detecting oscillation in the servo system, particularly, oscillation in the servo system caused by resonance in the servo system which includes a mechanical system, and in an adjustment mode in which the speed loop gain is automatically adjusted.

The operation of the numerical control unit is explained below.

When the initial values fn0, $\xi$0 and "0" of a cut-off frequency fn, damping factor $\xi$ and parameter P are set by an operator's operation, the processor of the numerical control unit causes a memory, accommodated in the processor, to store the initial values of the cut-off frequency fn, damping factor $\xi$ and parameter P. Then, the processor calculates the initial values of loop gains k1, k2 in accordance with the equations (1) and (2), stores these values, and initializes a flag F and the value of an index i, mentioned later, to "0".

Next, the processor repeatedly executes the speed control loop process and actual motor speed detection process of FIG. 5 at intervals of a predetermined period, when the detection mode is selected by an operator's operation.

At first, the processor determines whether or not the flag F is set to the value of "1" which indicates the completion of the actual motor speed detection process (step 100). If the flag F is not set to the value "1", the processor converts a first speed command Vc(in) obtained in the proportional term 1 of the position control loop into a second speed command Vc(out) in the same manner as in the first embodiment. That is, the processor reads out the first speed command Vc(in) (step 101), and determines whether or not the value is equal to or larger than zero (step 102). Next, the second speed command Vc(out) is calculated in accordance with the equation (3) or (4) in dependence on the determination result, and is stored in the memory of the processor (step 103).

Then, the processor reads a speed signal Vt indicative of the actual rotation speed of the servomotor (step 105), causes the memory to store the signal Vt at its memory address Mi corresponding to the index i (step 106), and then increments the index i by "1" (step 107). Next, it determines whether or not the index i is larger than a set value N which indicates that number (the power of 2) of speed signal data which is necessary for the later-mentioned frequency analysis (step 108). If the index i is not larger than the set value N, the speed control loop process based on the speed command Vc(out) is carried out(step 110), to derive a torque command, whereby the process of FIG. 5 in the present period is completed. Then, a current control loop process (not shown) is entered to drive and control the servomotor.

Whereupon, the process of FIG. 5 is repeatedly executed, and the speed signal Vt is periodically detected and stored in a corresponding address i of the memory. During this time, the servomotor rotates in forward and reverse directions in an oscillating fashion, like the first embodiment. Namely, the servomotor rotates in the forward direction in response to the positive command Vc(out), if the first speed command Vc(in) or the position deviation is equal to or larger than zero at the starting time (first period) of the speed control loop process, and, in the next period, rotates in the reverse direction in response to the negative command Vc(out) corresponding to the negative position deviation. Thereafter, the servomotor is rotated alternately in the forward and reverse directions. Meanwhile, if the position deviation at the starting time of the speed control loop process is negative, the servomotor is rotated in the reverse direction, and then alternately rotated in the forward and reverse directions.

When it is determined at step 108 that the index i has exceeded the set value N while the speed control loop process and actual motor speed detection process are repeatedly executed, the processor sets, at step 109, the flag F to the value "1" which indicates the completion of the actual motor speed detection process (storage of N speed signal data), and then step 110 is entered. After completion of the actual speed detection process, only the speed control loop process of step 110 in FIG. 5 is periodically executed.

With reference to FIG. 6, the oscillation detection process performed by the processor will be explained. This oscillation detection process is periodically effected together with the aforementioned position control loop process, speed control loop process and current control loop process in a time period other than time periods where these processes are executed.

In the oscillation detection process of FIG. 6, the processor first determines whether or not the value of the flag F is equal to "1" (step 200), and if the flag F is not equal to "1" which indicates completion of the actual motor speed detection process, it does not execute the process of FIG. 6 in practice. On the other hand, if it is determined at step 200 that the value of the flag F is "1", the processor reads out N (power of 2) speed signal data respectively from the addresses M0 to Mn of the memory, and carries out frequency analysis such as a high-speed Fourier transformation for the data group (step 201), to derive the amplitudes of various frequency components of the speed signal data group (actual motor speed). In this case, a commercially available application software for high-speed Fourier transformation may be used.

Next, the processor determines the maximum value of the calculated amplitudes, and determines that frequency component which has the maximum amplitude among the various frequency components of the actual motor speed, i.e., the main oscillation component fmax (step 202). Further, it determines whether or not the stored value R(f) of a register, accommodated in the processor, is equal to "0" (step 203). This register, used to store the main oscillation component fmax, is set to a value "0", at initial setting. Therefore, the register value R(f) is determined as being "0" at step 203, and the processor causes the register to store the main oscillation component fmax derived in step 202 (step 205), and then adds a predetermined value fs to the currently set cut-off frequency fn, to thereby update the cut-off frequency fn (step 206). Next, the processor calculates the gains k1 and k2 in accordance with the equations (1), (2) on the basis of the updated cut-off frequency fn, and stores therein these calculated gains (step 207). Then, the index i and flag F are respectively reset to the value "0" (step 208), whereby the oscillation detection process in the first period is completed.

When the flag F is reset to the value "0" upon completion of the aforementioned oscillation detection process, the actual motor speed detection process of FIG. 5 is started again, and the speed control loop process of FIG. 5 is executed in accordance with the gains k1 and k2 newly calculated at step 207 of the oscillation detection process. Whereupon, the above two processes of FIG. 5 are periodically executed, and N actual speed signal data Vt are stored into the memory addresses M0 to Mn while the gains are updated, and then each time the flag F is set to the value "1", the oscillation detection process of FIG. 6 is started again. In this case, the processor determines at step 203 that the register value R(f) is not "0", and then determines whether or not the main oscillation component fmax newly derived at step 202 is equal to or larger than the product of the register value R(f) and a predetermined value m (=2 to 3) (step 204). If the main oscillation component fmax is smaller than the product m·R(f), the processor executes the process of step 205 and the succeeding steps, to thereby update the gains k1 and k2. Then, the oscillation detection process of FIG. 6 in the present period is completed, and the actual motor speed detection process of FIG. 5 is executed.

As described above, if it is determined at step 204 of FIG. 6 that the main oscillation component fmax is equal to or larger than the product m·R(f) while the processes of FIGS. 5 and 6 are periodically and alternately executed, then the processor determines that the servo system has resonated and oscillation has occurred in the servo system as the result that the setting values of the speed control loop gains determined in accordance with the gains k1 and k2 have become excessively large. That is, when the servo system including a mechanical system has resonated, the main oscillation component fmax of the actual motor speed is generally increased to a considerably large value which is several times larger than a value which can be assumed in a case other than the resonant state.

Apparently, the loop gain which causes oscillation in the servo system is inappropriate. Thus, if it is determined at step 204 that oscillation has occurred in the servo system, the processor causes a display unit (not shown) of the numerical control unit to display the current values of the gains k1 and k2, cut-off frequency fn and main frequency component fmax for warning (step 209), and completes the oscillation detection process.

Next, an automatic speed loop gain adjusting process periodically effected by the numerical control unit of the second embodiment will now be described with reference to FIG. 7.

When the gain adjusting mode is selected by an operator's operation, the processor of the numerical control unit first executes the aforementioned speed control loop and actual motor speed detection processes of FIG. 5. Thereafter, when the actual motor speed detection process for periodically extracting and storing N speed signal data Vt is completed and the flag F is set to the value "1" at step 109 of FIG. 5, the gain adjusting process of FIG. 7 is periodically executed instead of the oscillation detection process of FIG. 6 which is executed upon selection of the detection mode.

More specifically, when it is determined at step 300 that the flag F is set to the value "1", the processor executes steps 301 and 302 corresponding to steps 201 and 202 of FIG. 6. Namely, the processor performs high-speed Fourier transformation for the N speed signal data stored in the memory, to derive the amplitudes of various frequency components of the data group and then determine the frequency component (main oscillation component) fmax having the maximum amplitude among the frequency components.

Next, the processor executes steps 303 to 308 corresponding to steps S5 to S9 and S2 of FIG. 4 relating to the first embodiment. That is, if the absolute value |fmax−fa| of the difference between the main oscillation component fmax and a reference frequency is not smaller than the threshold value $\epsilon$, the currently set cut-off frequency fn is updated to the sum [fn+α(fa−fmax)] of the just-mentioned set frequency and the product of an arithmetic coefficient and a value obtained by subtracting the main oscillation component from the reference frequency. Then, if it is determined that the set cut-off frequency fn is not smaller than the upper limit $f_{lim}$ of the frequency band of the speed control loop and the the parameter P has the value of "0", the processor changes the parameter P to the value "1" and resets the set cut-off frequency to the initial value fn0, and then derives the gains k1 and k2 in accordance with the equations (1) and (2). Upon completion of the gain calculation step 308, the processor resets the index i and flag F to the value "0" (step 309), and completes the gain adjusting process in the present period.

As a result, the actual motor speed detection process (steps 101 to 108) of FIG. 5 is started again, whereas the gain adjusting process of FIG. 7 is interrupted until the detection process is completed. When the detection process of FIG. 5 is completed, the gain adjusting process is started again. In this way, the detection process and gain adjusting process are alternately and periodically effected. Thereafter, if it is determined at step 303 that the absolute value |fmax−fa| of the difference between the main oscillation component and the reference frequency is smaller than the threshold value $\epsilon$, the gain adjustment is completed, so that the stored values of the gains k1, k2 and the parameter P at the instant at which the aforesaid determination is made are fixedly set, as the gains and the parameter. On the other hand, after the parameter P is changed to the value "1" and when the set cut-off frequency fn exceeds the upper limit $f_{lim}$ before the absolute value |fmax−fa| becomes smaller than the threshold value $\epsilon$, the set cut-off frequency fn is changed to the upper limit $f_{lim}$ (step 310) in the same manner as in the first embodiment, and the gains k1 and k2 are calculated based on this value $f_{lim}$ (step 311). As a result, like the first embodiment, the gains k1 and k2 and the parameter P are optimized.

Figure 8:
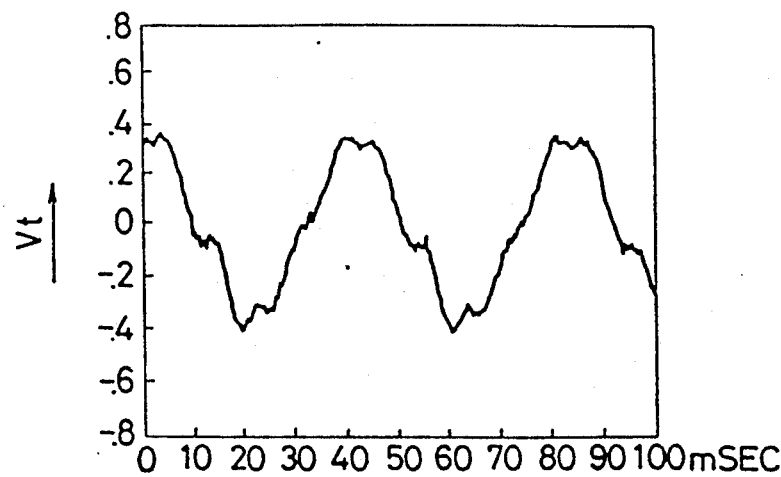
FIG. 8 is a waveform diagram of an actual motor speed, which is associated with the second embodiment.

FIG. 8 shows a waveform of the actual motor speed for the case where the speed control loop gain is so adjusted that the main oscillation component fmax of 25 Hz (period of 40 msec) appears in the machine having a mechanical resonance frequency of 120 Hz (period of approximately 8 msec).

Figure 9:
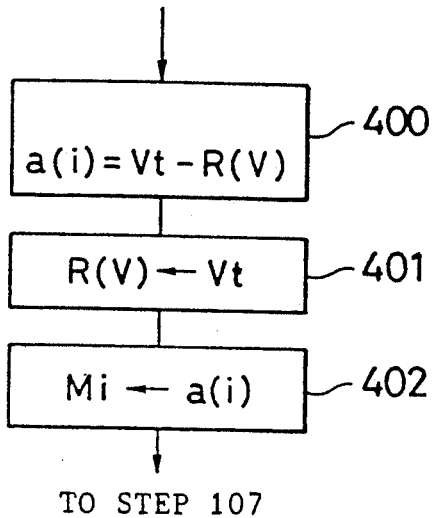
FIG. 9 is a flowchart illustrating an actual motor acceleration detection process according to a third embodiment of the present invention.

With reference to FIG. 9, an oscillation detection method and automatic speed control loop gain adjusting method for the servo system according to a third embodiment of the present invention will be described.

The method of the present embodiment is characterized in that the oscillation of the servo system caused by the resonance of the mechanical system can be detected at an early stage. To this end, the processor of the numerical control unit periodically is arranged to execute various processes which are basically the same as the processes shown in FIGS. 5 to 7 in the second embodiment, and at the same time execute steps 400 to 402 of FIG. 9 instead of step 106 of FIG. 5. In other words, the processor performs an actual motor acceleration detection process instead of the actual motor speed detection process.

More specifically, in the acceleration detection process and in the speed control loop process, the processor executes steps 100 to 105 of FIG. 5, and then subtracts a stored value R(v), detected in the preceding period and stored in the register, from actual speed data Vt indicative of the actual speed, detected in each period of the detection process, to thereby derive acceleration signal data a(i) (step 300). Then, the register value R(v) is updated to the value Vt detected in the current period (step 401), and the acceleration signal data a(i) is stored into a corresponding address Mi of the memory (step 402). Meanwhile, the register is reset to a value of "0" upon initial setting. Then, step 107 and the succeeding steps of FIG. 7 are executed.

When N acceleration signal data are stored into the memory addresses M0 to Mn while the above actual motor acceleration detection process and speed control loop process are repeated, the processor sets the flag F to a value of "1".

Upon inversion of the value of the flag F from "0" to "1" while the numerical control unit is operated in the oscillation detection mode, the processor performs substantially the same oscillation detection process as that shown in FIG. 4, except that the index i and flag F are reset to the value "0" and at the same time the value R(v) of a speed signal data storage register is reset to a value of "0", at step 208.

As described above, since the oscillation detection process is effected in dependence on the actual acceleration instead of the actual speed, the oscillation of the mechanical system caused by the resonance of the mechanical system can be detected at an early stage. The reason therefor will be explained below.

In general, the mechanical system controlled by the servo system has its resonant frequency which is several times the fundamental oscillation frequency f0 generated in the servo system when the servomotor rotates in the forward and reverse directions in an oscillating fashion, as described above. Thus, the resonant frequency of the mechanical system is represented by mf0 (m is a positive integer). Then, the actual servomotor speed V is represented as a function of time t, fundamental oscillation frequency f0 and resonant frequency mf0, as shown in the following equation (5), and the actual motor acceleration $\omega(t)$ is represented by the following equation (6) obtained by differentiating both sides of the equation (5).

$$V(t) = A1 \cdot \sin(2\pi f0 \cdot t) + A2 \cdot \sin(2\pi mf0 \cdot t + \rho) \quad (5)$$

$$\omega(t) = dV(t)/dt = 2\pi f0 \cdot A1 \cdot \cos(2\pi f0 \cdot t) + 2\pi mf0 \cdot A2 \cdot \cos(2\pi mf0 \cdot t + \rho) \quad (6)$$

where $\rho$ denotes a phase lag.

The ratio mA2/A1 of the amplitude of the second term to the amplitude of the first term on the right side of the equation (6) is m times the ratio A2/A1 of the amplitude of the second term to the amplitude of the first term on the right side of the equation (5). In other words, the degree of contribution of the resonance frequency mf0 to variation in the actual motor acceleration is larger than the degree of contribution to the variation in the actual motor speed. Therefore, according to the method of the third embodiment in which the acceleration signal data a(i) is subjected to the frequency analysis, oscillation of the servo system caused by the resonance of the mechanical system can be detected at an earlier stage, in which influence of the resonance of the mechanical system on the oscillation of the servo system is not significant, as compared with the method of the second embodiment where the speed signal data Vt is subjected to the frequency analysis.

Figure 10:
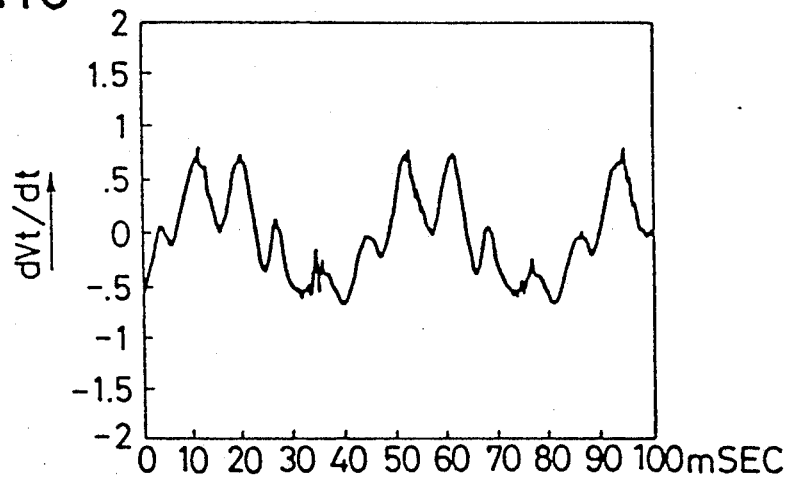
FIG. 10 is a waveform diagram of an actual motor acceleration, associated with the third embodiment.

FIG. 10 shows a waveform of the actual motor acceleration observed when the speed control loop gain is so adjusted that the main oscillation component fmax of 25 Hz (period of 40 msec) appears in a machine having a mechanical resonance frequency of 120 Hz (period of 8 msec).

Now, an oscillation detection method and automatic speed control loop gain adjusting method for the servo system according to a fourth embodiment of the present invention will be explained.

The method of the present embodiment is characterized in that an offset value for determining the position deviation-to-position control loop gain characteristic curve of a function generator 2 can be variably set, in the oscillation detection process, in dependence on the main oscillation component.

The reason for variably setting the offset value will be explained below.

Figure 11:
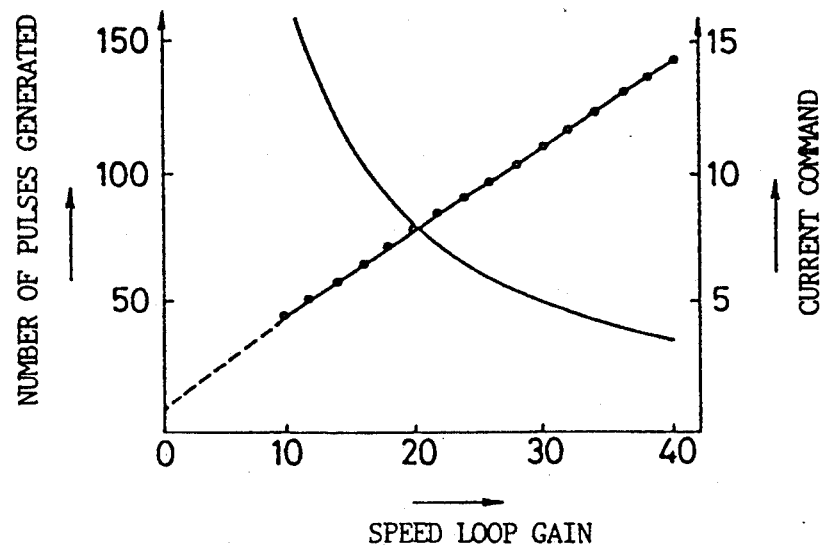
FIG. 11 is a diagram showing a speed loop gain-to-current command characteristic curve and a loop gain-to-offset value determination curve.

If a rotational displacement (oscillation amplitude) of the motor, during the motor rotation in forward and reverse directions in an oscillating fashion, is excessively small so that a relative displacement between associated component parts of the mechanical system, corresponding to the rotational displacement, is smaller than an amount of backlash, or if friction, e.g., friction torque, occurring in the mechanical system during the motor rotation is large, the motor rotation (stick slip) is obstructed. In particular, the aforementioned phenomenon becomes significant, if the speed loop gain is small and hence the rise of the torque command is delayed. In order to make the relative displacement between the machine component parts larger than the amount of backlash, or increase the motor rotation torque, so as to eliminate the aforesaid phenomenon, it is necessary to increase the offset value of FIG. 3 which determines the position loop gain at points near the position deviation of "0" in the motor oscillating operation. Particularly, when the frequency band of the speed control loop is shifted towards a low frequency range and the speed loop gain is small, the offset value must be increased, as shown by a gain-to-generated pulse number (offset value) characteristic indicated by a solid line in FIG. 11.

On the other hand, if the motor oscillation amplitude or oscillation speed is excessively large, in other words, if the torque command (motor output torque) is excessively large, the torque command is limited by a torque limit value and is saturated, causing the motor to generate heat or causing the mechanical system to vibrate. According to the experiments conducted by the inventors, a current command (torque) increases with an increase in the speed loop gain, as indicated by the gain-to-torque characteristic with open circles in FIG. 11. Thus, the aforesaid problem becomes serious when the speed loop gain is large. To obviate this, particularly in case that the frequency band of the speed control loop lies in the high frequency range, the offset value must be reduced as shown by the solid line in FIG. 11.

After all, it is necessary to increase the offset value when the frequency band of the speed control loop lies in the low frequency range and reduce the same when it lies in the high frequency range. In the present embodiment, in view of the fact that the frequency band of the speed control loop corresponds to the main oscillation component fmax of the actual motor speed, the offset value is derived by dividing a predetermined value B by the main oscillation component fmax, and an estimated value is used as the initial value of the main oscillation component fmax.

Figure 12:
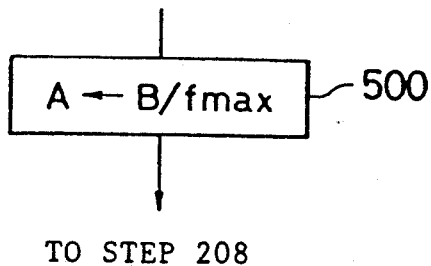
FIG. 12 is a diagram showing an offset value calculation step in a fourth embodiment of the present invention.

With reference to FIG. 12, the operation of the numerical control unit for embodying the method of the present embodiment will be described.

The processor of the numerical control unit periodically performs various processes which are basically the same as those shown in FIGS. 5 to 7, and causes a memory to store the initial value of the main oscillation component fmax and a predetermined value B when these values are set by the operator prior to the start of the various processes. Further, the processor executes the offset value calculating step 500 of FIG. 12 between steps 207 and 208 of the oscillation detection process of FIG. 6.

At step 500 of the oscillation detection process in a first period, the processor reads out the predetermined value B and the initial value of the main oscillation component fmax from the memory, derives an offset value A in a positive position deviation range by dividing the predetermined value B by the initial value, and then derives an offset −A in a negative position deviation range by inverting the sign thereof. Further, in the offset value calculation step 500 in a second and later periods, the main oscillation component fmax determined at step 202 in each period is used instead of the initial value of the main oscillation component fmax. As a result, the absolute values of the offset values A and −A derived at step 500 becomes smaller with an increase in the speed loop gain.

The present invention is not limited to the first to fourth embodiments, and may be modified in various manners.

For example, in each of the foregoing embodiments, the speed signal Vt is used as the position deviation parameter for the automatic speed loop gain adjustment, but a position deviation amount may be used instead of the speed signal Vt when a position command of zero is delivered during the motor oscillation.

Further, it is possible to combine the third embodiment capable of detecting oscillation of the servo system at an early stage in dependence on the motor acceleration with the fourth embodiment variably setting the offset value in dependence on the main oscillation component fmax, thereby optimizing the speed loop gain. In this case, steps 400 to 402 of FIG. 9 are executed instead of step 106 of FIG. 5, so as to determine the main oscillation component fmax in accordance with the acceleration signal a(i), and derive the offset value in dependence on the main oscillation component fmax.

In the gain adjustment process (FIG. 7) of the second and fourth embodiments, the offset value may be variably set as in the oscillation detection process (FIG. 12) of the fourth embodiment. In this case, step 500 of FIG. 12 is executed between steps 308 and 309 of FIG. 7.

Further, in the gain adjustment process (FIG. 7) of the second to fourth embodiments, it is possible to make warning that oscillation of the servo system has occurred due to the resonance of the mechanical system, as in the oscillation detection process (FIG. 6) of the second embodiment. In this case, steps 203, 204 and 209 of FIG. 6 are executed between steps 302 and 303 of FIG. 7.

I claim:

1. A method of automatically adjusting a speed loop gain of a servo system, comprising the steps of:
   (a) setting a position deviation-to-position loop gain characteristic of the servo system such that the position loop gain of the servo system assumes a large value in a predetermined position deviation range;
   (b) periodically extracting a position deviation parameter generated when the servo system is operated in accordance with a position command falling within the predetermined position deviation range;
   (c) determining a main oscillation component of the position deviation parameter; and
   (d) automatically adjusting the speed loop gain of the servo system such that the main oscillation component falls with a predetermined frequency range.

2. A method according to claim 1, wherein the predetermined position deviation range is so set as to include a range in which the position deviation assumes a value close to zero.

3. A method according to claim 1, wherein a position command having a value of zero is delivered in said step (b).

4. A method according to claim 1, wherein the position deviation parameter comprises a speed signal indicative of an actual speed of a servomotor driven by said servo system.

5. A method according to claim 1, wherein the main oscillation component is determined by effecting a frequency analysis with respect to the position deviation parameter in said step (c).

6. A method according to claim 5, wherein amplitude of various frequency components of the position deviation parameter are detected in the frequency analysis, and that one of the various frequency components which has a maximum amplitude is determined as the main frequency component.

7. A method according to claim 6, wherein the extracted position deviation parameter is differentiated, and then the main oscillation component of the differentiated position deviation parameter is determined, in said step (b).

8. A method according to claim 1, wherein an offset value of the deviation-to-position loop gain characteristic curve for determining the position loop gain in the predetermined deviation range is set variably such that it is inversely proportional to the main oscillation component.

9. A method of detecting an oscillation of a servo sytem, comprising the steps of:
   (a) setting a position deviation-to-position loop gain charateristic of the servo system so that the position loop gain of the servo system assumes a large value in a predetermined position deviation range;
   (b) periodically extracting a position deviation parameter generated when the servo system is operated in accordance with a position command falling within the predetermined deviation range;
   (c) determining a main oscillation component of the position deviation parameter;
   (d) increasing the speed loop gain of said servo system, and then executing said steps (b) and (c); and
   (e) automatically determining that oscillation has occurred in said servo system when the main oscillation component has rapidly increased.

10. A method according to claim 9, wherein the extracted position deviation parameter is differentiated and then the main oscillation component of the differentiated position deviation parameter is determined, in said step (c).

11. A method according to claim 9, wherein an offset value of the position deviation-to-position loop gain characteristic curve for determining the position loop gain in the predetermined deviation range is set variably such that it is inversely proportional to the main oscillation component.

12. A method according to claim 10, wherein an offset value of the position deviation-to-position loop gain characteristic curve for determining the position loop gain in the predetermined deviation range is set variably such that it is inversely proportional to the main oscillation component.

* * * * *

UNITED STATES PATENT AND TRADEMARK OFFICE
CERTIFICATE OF CORRECTION

PATENT NO. : 5,157,597

DATED : October 20, 1992

INVENTOR(S) : Iwashita

It is certified that error appears in the above-identified patent and that said Letters Patent is hereby corrected as shown below:

Col. 14, line 26, after "the" insert --position--.

Signed and Sealed this

Fifth Day of October, 1993

Attest:

BRUCE LEHMAN

Attesting Officer

Commissioner of Patents and Trademarks